US008003353B2

(12) United States Patent
Quay et al.

(10) Patent No.: US 8,003,353 B2
(45) Date of Patent: *Aug. 23, 2011

(54) CYANOCOBALAMIN LOW VISCOSITY AQUEOUS FORMULATIONS FOR INTRANASAL DELIVERY

(75) Inventors: Steven C. Quay, Edmonds, WA (US); Peter C. Aprile, East Northport, NY (US); Zenaida O. Go, Clifton, NJ (US); Anthony P. Sileno, Brookhaven Hamlet, NY (US)

(73) Assignee: Par Pharmaceutical, Inc., Woodcliff Lake, NJ (US)

( * ) Notice: Subject to any disclaimer, the term of this patent is extended or adjusted under 35 U.S.C. 154(b) by 381 days.

This patent is subject to a terminal disclaimer.

(21) Appl. No.: 12/142,240

(22) Filed: Jun. 19, 2008

(65) Prior Publication Data

US 2008/0255067 A1    Oct. 16, 2008

Related U.S. Application Data

(60) Division of application No. 10/814,399, filed on Mar. 31, 2004, now Pat. No. 7,404,489, which is a continuation-in-part of application No. 10/787,385, filed on Feb. 26, 2004, now Pat. No. 7,229,636.

(60) Provisional application No. 60/451,899, filed on Mar. 4, 2003, provisional application No. 60/461,583, filed on Apr. 8, 2003, provisional application No. 60/474,204, filed on May 29, 2003.

(51) Int. Cl.
C12P 19/42 (2006.01)
A61K 31/70 (2006.01)
A01N 43/04 (2006.01)
C07H 19/20 (2006.01)

(52) U.S. Cl. .............................. 435/86; 514/52; 536/26.4
(58) Field of Classification Search .................. 424/434, 424/1.73; 514/52; 435/86; 536/26.4
See application file for complete search history.

(56) References Cited

U.S. PATENT DOCUMENTS

| 2,703,302 A | 3/1955 | Rickes et al. |
| 2,703,303 A | 3/1955 | Rickes et al. |
| 2,746,796 A | 5/1956 | Germain et al. |
| 2,914,222 A | 11/1959 | Meshberg |
| 2,951,017 A | 8/1960 | Speedie et al. |
| 3,000,793 A | 9/1961 | McDaniel |
| 3,018,225 A | 1/1962 | Long |
| 3,057,851 A | 10/1962 | Van Melle |
| 3,120,508 A | 2/1964 | Braun et al. |
| 3,120,509 A | 2/1964 | Bernhauer et al. |
| 3,282,781 A | 11/1966 | Macek et al. |
| 3,548,057 A | 12/1970 | Kelley et al. |
| 3,577,537 A | 5/1971 | Howe et al. |
| 3,584,115 A | 6/1971 | Gebhart et al. |
| 3,957,968 A | 5/1976 | Cordon |
| 4,174,295 A | 11/1979 | Bargigia et al. |
| 4,523,341 A | 6/1985 | Queen |
| 4,525,341 A | 6/1985 | Deihl |
| 4,724,231 A | 2/1988 | Wenig |
| 4,727,231 A | 2/1988 | Hayano et al. |
| 4,959,176 A | 9/1990 | Slocum et al. |
| 5,277,311 A | 1/1994 | Kuemmerle et al. |
| 5,797,390 A | 8/1998 | McSoley |
| 5,801,161 A | 9/1998 | Merkus |
| 5,825,625 A | 10/1998 | Esterberg et al. |
| 5,925,625 A | 7/1999 | Merkus |
| 6,406,730 B1 | 6/2002 | Banyard et al. |
| 6,665,421 B1 | 12/2003 | Farina |
| 6,685,421 B1 | 2/2004 | Reeves |
| 6,745,760 B2 | 6/2004 | Grychowski et al. |
| 6,911,434 B2 | 6/2005 | Baldridge et al. |
| 2004/0043043 A1 | 3/2004 | Schlyter et al. |
| 2004/0109826 A1 | 6/2004 | Malladi et al. |
| 2006/0046969 A1 | 3/2006 | Maggio |
| 2006/0074034 A1 | 4/2006 | Collins et al. |
| 2006/0105432 A1 | 5/2006 | Barg et al. |
| 2006/0127320 A1 | 6/2006 | Costantino et al. |

FOREIGN PATENT DOCUMENTS

| CA | 1317881 | 5/1993 |
| EP | 0131315 A2 | 2/1984 |
| EP | 0130550 A2 | 6/1984 |
| WO | WO 86/05987 | 10/1986 |
| WO | WO 86/05988 | 10/1986 |

OTHER PUBLICATIONS

Allen, 2002, "Prescription", Intl. J. of Pharmaceutical Compounding, vol. 6(3): 208.

Anwar et al., 1984, "Studies on the intranasal absorption of Vitamin $B^{12}$ in the rat," Final Report, Dec. 1984, University of Kentucky, College of Pharmacy, Lexington, KY.

Chandra et al., 1982, "Double-blind controlled crossover trial of 4% intranasal sodium crymoglycate solution in patients with seasonal allergic rhinitis," Annals of Allergy, vol. 49, from the Dept. of Pediatrics, Memorial University of Newfoundland, Janeway Child Health Center and Health Sciences Center. St. John's, Newfoundland, Canada.

(Continued)

Primary Examiner — Paul V. Ward
(74) Attorney, Agent, or Firm — Arent Fox LLP

(57) ABSTRACT

A stable pharmaceutical mercury-free aqueous solution of cyanocobalamin comprised of cyanocobalamin and water wherein said solution of cyanocobalamin is suitable for intranasal administration, has a viscosity less than about 1000 cPs, and wherein said solution of cyanocobalamin has a bioavailability of cyanocobalamin when administered intranasally of at least about 7% relative to an intramuscular injection of cyanocobalamin with the proviso that the solution is essentially free of mercury and mercury-containing compounds. The present invention is also directed towards a method for elevating the vitamin B12 levels in the cerebral spinal fluid (CSF) comprising administering intranasally a sufficient amount of a mercury-free cyanocobalamin solution so as to increase the average ratio of vitamin B12 in the CSF to that in the blood serum (B12 CSF/B12 Serum×100) to at least about 1.1 comprising intranasally administering an aqueous solution of a cyanocobalamin, wherein said solution of cyanocobalamin has a bioavailability of at least 7% relative to an intramuscular injection of a cyanocobalamin.

6 Claims, 1 Drawing Sheet

OTHER PUBLICATIONS

Chen et al., 1983, Characterization of dose delivery and spray pattern of a metered-dose flunisolide nasal spray, Drug development and industrial pharmacy, vol. 9(3):473-483, Institute of Pharmaceutical Sciences, Syntex Research, Palo Alto, CA Mercel Dekker, Inc.

Cutie et al., 1982, "Intranasal pharmaceutical aerosols, aerosal age, the international authority in spray packaging," Aerosol Age Magazine, Oct. 1982, pp. 1-4.

Edited by James E.F. Reynolds, Cyanocobalamin, Martindale, The Extra Pharmacopoeia, 1982, Abstract 7853-d, and p. 1645. Cyanocobalamin Injection, 28th Edition. Published by direction of the Council of The Pharmaceutical Society of Great Britain and prepared in the Society's Dept. of Pharmaceutical Sciences, The Pharmaceutical Press, London, UK.

Forest Laboratories, Inc., 1972 "Long acting oral carrier," Chemical Abstracts, vol. 77, p. 263, Abstract 105623(y).

Garcia-Arieta et al., 2001, "Spray-dried powders as nasal absorption enhancers of cyanocobalamin," Biol. Pharm. Bull., vol. 24(2):1411-1416.

Harris et al., 1988, "Effect of viscosity on particle size, deposition, and clearance of nasal delivery systems containing desmopressin," J. Pharm Sci., vol. 77(5):405-408.

Killander et al., 1961, "Studies on maintenance treatment of pernicious anaemia, Vitamin $B^{12}$ and instrinsic factor," Europaisches Symposian Hamburg, pp. 663-687, Ed. H.c. Heinrich, Enke, Stuttgart, Dept. of Pediatris and Internal Medicine, Akademiska,Sjukhuset, Uppsala, Sweden.

Mathison et al., 1998, "Nasal route for direct delivery of solutes to the central nervous system: Fact or fiction?" J. of Drug Targeting, vol. 5(6):415-441.

Monto et al., 1953, "Crystalline $B^{12}$ inhallation therapy in pernicious anemia," The American Journal of the Medical Sciences, vol. 2, pp. 113-119, Publisher, Division of Hematology and Department of Laboratories, The Henry Ford Hospital, Detroit, Michigan.

Monto et al., 1954, "Nasal instiliation and inhalation of crystalline Vitamin $B^{12}$ in pernicious anemia," A.M.A. Archives 6 Internal Medicine, vol. 93:219-230, Division of Hematology (Dr. Monto) and the Dept of Laboratories (Dr. Rebuk), The Henry Ford Hospital.

Monto et al., 1955, "Observations on the mechanism of intranasal absorption of Vitamin $B^{12}$ in pernicious anemia," Blood, vol. 10:1151-1155.

Nijst et al., 1990, "Vitamin $B^{12}$ and folate concentrations in serum and cerebrospinal fluid of neurological patients with special reference to multiple sclerosis and dementia," J. of Neurology, Neurosurgey and Psychiatry, vol. 53:951-954.

Shinton et al., 1967, "Vitamin $B^{12}$ absorption by inhalation," Brit J. Haematol., vol. 13:75-79.

Shinton et al., 1967, "Vitamin $B^{12}$ absorption by inhalation," Chemical Abstracts, vol. 66, No. 15, Coden: Chaba8, The American Chemical Society , p. 6024, Abstract 64246(2).

Siarra, J.J. Aerosols, Chapter 92, year unknown, pp. 1614-1621, Arnold & Marie Schwartz, Collet of Pharmacy and Health Sciences, Long Island University, Brooklyn, NY.

Slot et al., 1997, "Normalization of plasma vitamin $B^{12}$ concentration by intranasal hydroxocobalamin in Vitamin $B^{12}$-defient patients," Gastro, vol. 113:430-433.

U.S. Department of Health and Human Services, (Draft) 2003. "Guidance for Industry, Bioavailability and Bioequivalence Studies for Nasal Aerosols and Nasal Sprays for Local Action," Apr. 2003, pp. 1-36 + attachments, U.S. FDA, Center for Drug Evaluation and Research, Biopharmaceutics.

U.S. Dept. of Health and Humans Services, 2002. "Guidance for Industry, Nasal spray and inhalation solution, suspension, and spray drug products-chemistry, manufacturing, and controls documentation," Jul. 2002, pp. 1-44, FDA, Center for Drug Evaluatio and Research.

Valois, "Pumps for Pharmacy," Year unknown (product brochure).

CYANOCOBALAMIN LOW VISCOSITY AQUEOUS FORMULATIONS FOR INTRANASAL DELIVERY

CROSS REFERENCE TO RELATED APPLICATIONS

This application is a division and claims priority under Title 35, U.S. Code, §120 of U.S. patent application Ser. No. 10/814,399 filed on Mar. 31, 2004 now U.S. Pat. No. 7,404,489, currently allowed, which is a continuation-in-part and claims priority under Title 35, U.S. Code, §120 of U.S. patent application Ser. No. 10/787,385 filed on Feb. 26, 2004, now U.S. Pat. No. 7,229,636 issued Jun. 12, 2007, which claims the benefit under 35 U.S.C. §119(e) of U.S. Provisional Application No. 60/451,899 filed on Mar. 4, 2003, U.S. Provisional Application No. 60/461,583 filed on Apr. 8, 2003, and U.S. Provisional Application No. 60/474,204 filed on May 29, 2003, each of which is incorporated by reference herein in its entirety.

BACKGROUND OF THE INVENTION

Vitamin B12 is a dietary essential, a deficiency of which results in defective synthesis of DNA in any cell in which chromosomal replication and division are taking place. Since tissues with the greatest rate of cell turnover show the most dramatic changes, the hematopoietic system is especially sensitive to vitamin B12 deficiencies. An early sign of B12 deficiency is a megaloblastic anemia. Dietary B12, in the presence of gastric acid and pancreatic proteases, is released from food and salivary binding protein and bound to gastric intrinsic factor. When the vitamin B12-intrinsic factor complex reaches the ileum, it interacts with a receptor on the mucosal cell surface and is actively transported into circulation. Adequate intrinsic factor, bile and sodium bicarbonate (suitable pH) all are required for ileal transport of vitamin B12. Vitamin B12 deficiency in adults is rarely the result of a deficient diet; rather, it usually reflects a defect in one or another aspect of this complex sequence of absorption. Achlorhydria and decreased secretion of intrinsic factor by parietal cells secondary to gastric atrophy or gastric surgery is a common cause of vitamin B12 deficiency in adults. Antibodies to parietal cells or intrinsic factor complex also can play a prominent role in producing deficiency. A number of intestinal diseases can interfere with absorption. Vitamin B12 malabsorption is seen with pancreatic disorders (loss of pancreatic protease secretion), bacterial overgrowth, intestinal parasites, sprue, and localized damage to ileal mucosal cells by disease or as a result of surgery. The recommended daily intake of vitamin B12 in adults is 2.4 µg.

There are four main forms of vitamin B12: cyanocobalamin: hydroxocobalamin, methylcobalamin and adenosylcobalamin. Methylcobalamin and adenosylcobalamin are unstable and damaged by light. They are therefore unsuitable for use in dietary supplements or pharmaceuticals and are not essential since they can be formed from cyanocobalamin or hydroxocobalamin within the body. The main form of vitamin B12 found in food is hydroxocobalamin. The main form used therapeutically and in nutritional supplements is cyanocobalamin, chosen because it is the most stable form and therefore easiest to synthesize and formulate.

Because deficiencies of vitamin B12 are generally caused by the inability of the vitamin to be absorbed in the small intestine due to a breakdown in the vitamin B12-intrinsic factor complex transport mechanism, vitamin B12 must therefore be administered systemically. Currently, therapeutic amounts of cyanocobalamin are administered by intramuscular or deep subcutaneous injection of cyanocobalamin. However; patients must return to the physician's office periodically to receive additional injections to maintain their levels of vitamin B12. However, an intranasal gel cyanocobalamin preparation, NASCOBAL® is currently being marketed in which cyanocobalamin is administered intranasally as maintenance vitamin B12 therapy. However, many patients find the consistency of the intranasal gel unpleasant and would prefer to have administered intranasally a low viscosity spray containing cyanocobalamin.

The prior art suggests that for vitamin B12 to be absorbed intranasally in therapeutically beneficial amounts, the concentration of the B12 in solution must either be greater that 1% by weight, see Merkus, U.S. Pat. No. 5,801,161 or be administered intranasally in a viscous gel, Wenig, U.S. Pat. No. 4,724,231 so that the gel remains in the nostril for an extended period of time. In fact Wenig states that B12 administered intranasally in a low viscosity solution is not in contact with the nasal mucosa long enough for a sufficient period of time to permit useful absorption. Wenig claims that most of the B12 is wasted if the solution has a low viscosity. Merkus developed intranasal formulations of hydroxocobalamin having a concentration of hydroxocobalamin greater than 1%, however hydroxocobalamin is not very stable and thus has a short shelve-life. Merkus chose hydroxocobalamin because cyanocobalamin is not soluble in an aqueous solution at concentrations greater than 1%.

U.S. Pat. No. 4,525,341, Deihl, discloses a method of administering vitamins intranasally but do not enable a specific formulation containing only cyanocobalamin. International Patent Application No. PCT/US86/00665, publication no. WO 86/05987, discloses nasal spray composition containing vitamin B12 as cyanocobalamin. However, the specific spray formulations all contained a mercury compound as a preservative, however the disclosure did require the presence of mercury compounds. Other preservatives were also mentioned including benzalkonium chloride and chlorobutanol. As was stated above, an intranasal gel containing cyanocobalamin, NASCOBAL®, is currently being produced and marketed by Nastech Pharmaceutical Company Inc. of Bothell, Wash. It is very effective in maintaining levels of vitamin B12 for patients who have been deficient in the past but have recovered their levels of B12 through intramuscular injections. However, a number of patients find the consistency of the gel unpleasant in their nose, and would prefer an intranasal formulation that has a lower viscosity and is free of mercury compounds. Thus, there is a need to produce a pharmaceutically stable aqueous solution of cyanocobalamin that has a low viscosity, is free of mercury compounds and has sufficient bioavailability to be used as a maintenance therapy for vitamin B12.

SUMMARY OF THE INVENTION

The present invention fills this need by providing for a stable pharmaceutical solution of cyanocobalamin suitable for intranasal administration, having a viscosity less than about 1000 cPs, wherein said intranasal solution of cyanocobalamin has a bioavailability of at least 7% of the bioavailability of an intramuscular injection of cyanocobalamin and is free of mercury compounds.

A preferred formulation is comprised of cyanocobalamin, citric acid, sodium citrate, and water wherein the viscosity is less than 1000 cPs, and wherein the solution of cyanocobalamin has a bioavailability of at least 8%, more preferably at least about 9, 10, 11, or 12% of the bioavailability of an intramuscular injection of cyanocobalamin.

Preferred compositions within the scope of this invention will contain a humectant to inhibit drying of the mucous membranes and to prevent irritation. Any of a variety of humectants can be used including but not limited to sorbitol, propylene glycol or glycerol. A preferred humectant is glycerin.

A preservative is generally employed to increase the shelf life of the compositions. Examples of preservative include but are not limited to benzyl alcohol, chlorobutanol and benzalkonium chloride. A preferred preservative is benzalkonium chloride. A suitable concentration of the preservative will be from 0.002% to 2.0% based upon the total weight, although there may be appreciable variation depending upon the agent selected.

A most preferred formulation has the concentration of cyanocobalamin at 0.5% (percent of total weight), citric acid 0.12%, sodium citrate 0.32%, glycerin 2.23%, benzalkonium chloride 0.02% and 96.79% water.

Another embodiment of the present invention is a method for administering cyanocobalamin comprised of infusing the nose with an aqueous solution of cyanocobalamin, wherein the solution of cyanocobalamin has a viscosity of less than 1000 cPs, and wherein said solution of cyanocobalamin has a bioavailability of at least about 7% relative to an intramuscular injection of cyanocobalamin. Preferably, the bioavailability is at least 8%, 9%, 11% or 12%.

The present invention is further directed towards a method for elevating the vitamin B12 levels in the cerebral spinal fluid (CSF) comprising intranasally administering a solution of cyanocobalamin so as to increase the average ratio of vitamin B12 in the CSF to that in the blood serum (B12 CSF/B12 Serum×100) to at least about 1.1, wherein said solution of cyanocobalamin has a bioavailability of at least 7% relative to an intramuscular injection of cyanocobalamin. In a more preferred embodiment the B12 CSF levels are increased so that the ratio of B12 in the CSF to the levels in the blood serum is at least 1.9.

The methods of present invention are further comprised of the cyanocobalamin solutions being administered into a nose of an individual through an actuator tip as a spray, wherein the spray preferably has one or more of the following properties: a spray pattern ellipticity ratio of from about 1.0 to about 1.4 when measured at a height of 3.0 cm from the actuator tip; or the spray produces droplets, less than about 5% of the droplets are less than 10 µm in size; the spray has a spray pattern major axis of about 35.3 mm and a minor axis of about 30.8 mm; 50% of the droplets produced by the spray are 26.9 µm or less in size; 90% of the droplets produced by the spray are 55.3 µm or less in size; or 10% of the droplets produced by the spray are 12.5 µm or less in size.

DETAILED DESCRIPTION OF THE INVENTION

Figure 2:
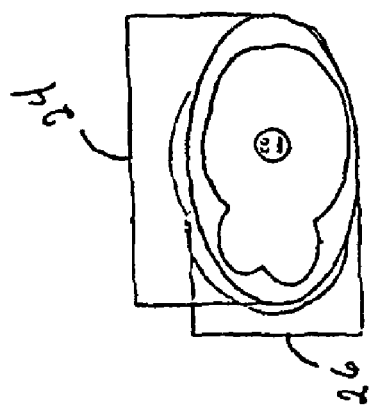
FIG. 2 shows the spray pattern produced by the actuator of the spray pump kit.

The following definitions may aid in the understanding of the present invention.

"About": is taken to be a relative term denoting an approximation of plus or minus 20% of the nominal value it refers to. For the field of pharmacology and clinical medicine and analogous arts that are the subject of this disclosure, this level of approximation is appropriate unless the value is specifically stated to be critical or to require a tighter range.

"Nasal mucosa": the nasal mucosa is taken to be the lining of the vestibule of the nose, where vascularized, and extending interiorly to the boundaries of the oropharynx and sinuses.

"Aqueous": refers to a solution formed in water, but may contain lesser amounts of other co-solvents.

"Bioavailability" is defined as the rate and extent to which the active ingredient or active moiety is absorbed from a drug product and becomes available at the site of action, [21 CFR §320.1(a)].

"Bioavailability of the intranasal spray relative to an intramuscular injection of cyanocobalamin" means the percent amount a dose of the intranasal taken up by the systemic vascular system in comparison to the same amount of cyanocobalamin injected. For example, assuming an intramuscular injection of a solution of cyanocobalamin containing 100 µg of cyanocobalamin would have a 100% bioavailability, if an intranasal dose of cyanocobalamin contains 100 µg and has at least 7% bioavailability relative to an injection of cyanocobalamin, at least 7 µg of cyanocobalamin would be taken up into the blood vasculature. Likewise, if the intranasal dose of cyanocobalamin contained 500 µg, at least 35 µg of cyanocobalamin would be taken up into the blood vasculature, if the intranasal formulation had a bioavailability of at least 7%.

"Stability": during storage, any compositional change measured in a parameter, examples of which include but are not limited to concentration, degradation, viscosity, pH, or particle size, that is considered to significantly affect the quality attributes of the product over time, denotes instability. In a similar vein, changes that are not considered to significantly affect the quality attributes of the product connote stability. The time period over which stability is measured is relative depending on the intended utility of the composition. Accelerated stability at higher temperature is sometimes taken as a more speedy way of extrapolating stability over longer periods of time than are actually measured.

"Pharmaceutically acceptable": refers to a composition which when administered to a human or a mammal by the indicated route of administration, provokes no adverse reaction which is disproportionate to the benefit gained by administration of said compound.

"Mammal" shall include any of a class of warm-blooded higher vertebrates that nourish their young with milk secreted by mammary glands and have skin usually more or less covered with hair, and non-exclusively includes humans and non-human primates, their children, including neonates and adolescents, both male and female, livestock species, such as horses, cattle, sheep, and goats, and research and domestic species, including dogs, cats, mice, rats, guinea pigs, and rabbits. "Patient" or "subject" is used herein interchangeably with "mammal."

"Intranasal delivery" shall mean delivery of a drug primarily via the mucosa of the nasal cavity. This includes the superior, middle and inferior nasal turbinates and the nasal pharynx. Note that the olfactory region is concentrated in the superior (upper ⅓) of the nasal turbinates. Cilial action pushes material back toward the oropharynx, so material deposited in the nasal vestibule encounters the nasal mucosa before entering the throat.

"Substantially free" refers to the level of a particular active ingredient in the compositions of the invention, wherein the particular active ingredient constitutes less than 20%, preferably less than 10%, more preferably less than 5%, and most preferably less than 1%, by weight based on the total weight of active ingredients in the composition.

Delivery vehicles herein found useful include actuator dispensers commonly used for nasal solutions and gels. Embodiments of this technology include multiple, single-dose, metered dose, child resistant, and disposable dispensers, and their kits.

As used herein "peak concentration ($C_{max}$) of cyanocobalamin in a blood plasma", "area under concentration vs. time curve (AUC) of cyanocobalamin in a blood plasma", "time to maximal plasma concentration ($t_{max}$) of vitamin in a blood plasma" are pharmacokinetic parameters known to one skilled in the art. [Laursen et al., *Eur. J. Endocrinology*, 135: 309-315, (1996)]. The "concentration vs. time curve" measures the concentration of cyanocobalamin in a blood serum of a subject vs. time after administration of a dosage of cyanocobalamin to the subject either by intranasal, subcutaneous, or other parenteral route of administration. "$C_{max}$" is the maximum concentration of cyanocobalamin in the blood serum of a subject following a single dosage of cyanocobalamin to the subject. The term "$t_{max}$" is the time to reach maximum concentration of cyanocobalamin in a blood serum of a subject following administration of a single dosage of cyanocobalamin to the subject.

As used herein, "area under concentration vs. time curve (AUC) of cyanocobalamin in a blood plasma" is calculated according to the linear trapezoidal rule and with addition of the residual areas. A decrease of 23% or an increase of 30% between two dosages would be detected with a probability of 90% (type II error $\beta=10\%$). The "delivery rate" or "rate of absorption" is estimated by comparison of the time ($t_{max}$) to reach the maximum concentration ($C_{max}$). Both $C_{max}$ and $t_{max}$ are analyzed using non-parametric methods. Comparisons of the pharmacokinetics of subcutaneous, intravenous and intranasal cyanocobalamin administrations were performed by analysis of variance (ANOVA). For pair wise comparisons a Bonferroni-Holmes sequential procedure was used to evaluate significance. The dose-response relationship between the three nasal doses was estimated by regression analysis. P<0.05 was considered significant. Results are given as mean values +/−SEM. (Laursen et al., 1996.)

The above-described cyanocobalamin solutions are designed to be administered to the nasal mucosa either in drop or in spray form. However, the preferred mode of administration is in spray form, i.e., in the form of finely divided droplets. An example of a suitable spray pump is the Pfeiffer Spray Pump Model # 63385 produced by Pfeiffer GmbH, Radolfzell, Germany.

Nasal Administration of Cyanocobalamin

Cyanocobalamin is administered intranasally using a nasal spray according to the present invention. In this area the following definitions are useful.

1. Aerosol—A product that is packaged under pressure and contains therapeutically active ingredients that are released upon activation of an appropriate valve system.
2. Metered aerosol—A pressurized dosage form comprised of metered dose valves, which allow for the delivery of a uniform quantity of spray upon each activation.
3. Powder aerosol—A product that is packaged under pressure and contains therapeutically active ingredients in the form of a powder, which are released upon activation of an appropriate valve system.
4. Spray aerosol—An aerosol product that utilizes a compressed gas as the propellant to provide the force necessary to expel the product as a wet spray; it generally applicable to solutions of medicinal agents in aqueous solvents.
5. Spray—A liquid minutely divided as by a jet of air or steam.
6. Metered spray—A non-pressurized dosage form consisting of valves that allow the dispensing of a specified quantity of spray upon each activation.
7. Suspension spray—A liquid preparation containing solid particles dispersed in a liquid vehicle and in the form of course droplets or as finely divided solids.

The fluid dynamic characterization of the aerosol spray emitted by metered nasal spray pumps as a drug delivery device ("DDD"). Spray characterization is an integral part of the regulatory submissions necessary for Food and Drug Administration ("FDA") approval of research and development, quality assurance and stability testing procedures for new and existing nasal spray pumps.

Thorough characterization of the spray's geometry has been found to be the best indicator of the overall performance of nasal spray pumps. In particular, measurements of the spray's divergence angle (plume geometry) as it exits the device; the spray's cross-sectional ellipticity, uniformity and particle/droplet distribution (spray pattern); and the time evolution of the developing spray have been found to be the most representative performance quantities in the characterization of a nasal spray pump. During quality assurance and stability testing, plume geometry and spray pattern measurements are key identifiers for verifying consistency and conformity with the approved data criteria for the nasal spray pumps.

DEFINITIONS

Plume Height—the measurement from the actuator tip to the point at which the plume angle becomes non-linear because of the breakdown of linear flow. Based on a visual examination of digital images, and to establish a measurement point for width that is consistent with the farthest measurement point of spray pattern, a height of 30 mm is defined for this study Major Axis—the largest chord that can be drawn within the fitted spray pattern that crosses the COMw in base units (mm)

Minor Axis—the smallest chord that can be drawn within the fitted spray pattern that crosses the COMw in base units (mm)

Ellipticity Ratio—the ratio of the major axis to the minor axis $D_{10}$—the diameter of droplet for which 10% of the total liquid volume of sample consists of droplets of a smaller diameter (μm)

$D_{50}$—the diameter of droplet for which 50% of the total liquid volume of sample consists of droplets of a smaller diameter (μm), also known as the mass median diameter $D_{90}$—the diameter of droplet for which 90% of the total liquid volume of sample consists of droplets of a smaller diameter (μm)

Span—measurement of the width of the distribution. The smaller the value, the narrower the distribution. Span is calculated as $$\frac{(D_{90}-D_{10})}{D_{50}}$$

% RSD—relative standard deviation, the standard deviation divided by the mean of the series and multiplied by 100, also known as % CV.

Cyanocobalamin Nasal Spray Kit.

The present invention is further comprised of a cyanocobalamin nasal spray kit and method of administering the cyanocobalamin solution using the nasal spray kit.

Figure 1B:
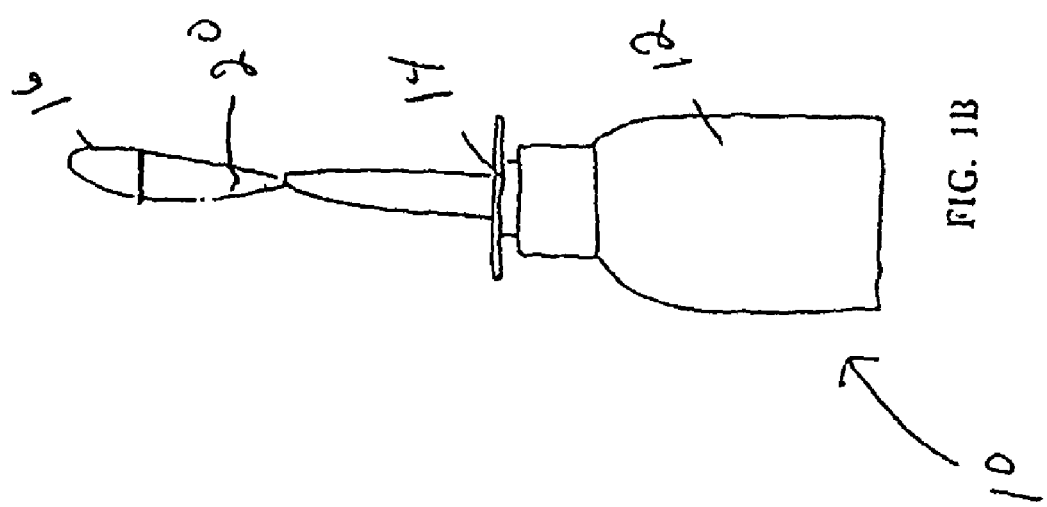
FIG. 1B shows the nasal spray pump kit containing the cyanocobalamin solution of the present invention having an actuator that is engaged and expelling a spray plume of the cyanocobalamin solution of the present invention.
Figure 1A:
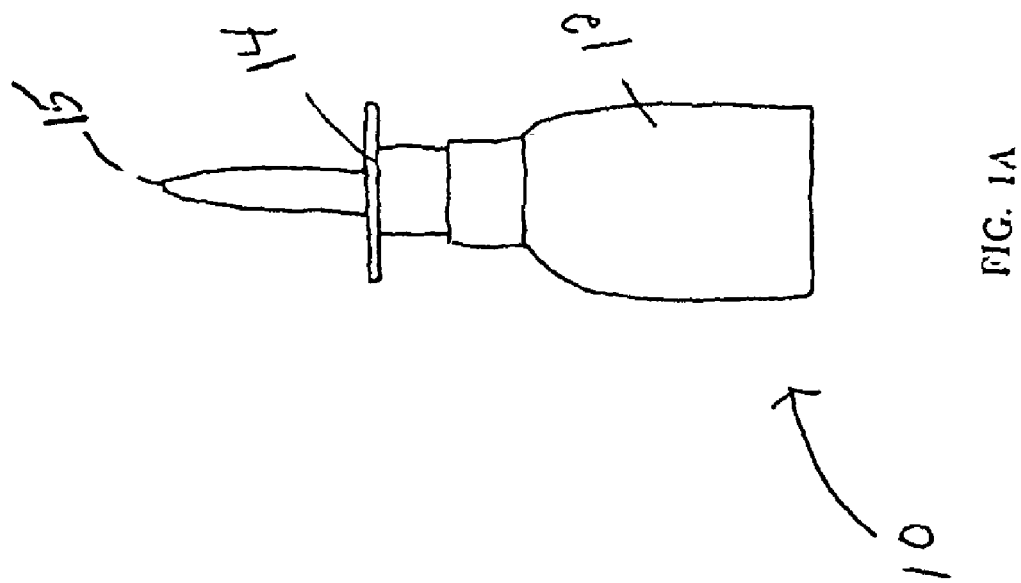
FIG. 1A shows a nasal spray pump kit containing the cyanocobalamin solution of the present invention having an actuator that is not engaged.

The nasal spray kit is exemplified by FIGS. 1A, 1B and FIG. 2. FIGS. 1A and 1B show a nasal spray device 10 before engagement (FIG. 1A) and after engagement (FIG. 1B). The cyanocobalamin nasal spray kit, 10, is comprised of a container, in this case a bottle 12 into which the cyanocobalamin formulation is placed, and an actuator 14, attached to bottle 12 and in fluid connection with the solution of cyanocobalamin in bottle 12. When the actuator, 14 is actuated or engaged, it forces a spray plume, 16 of cyanocobalamin through tip 15 of the actuator. The spray plume is comprised of droplets of the solution of cyanocobalamin. A spray pattern is determined by taking a photograph of a cross-section of the spray plume 16 above a predetermined height, of the plume. The spray plume also has angle of ejection, 20, as it leaves actuator, 14. A spray pattern of spray plume 16 is shown on FIG. 2. The Spray pattern of FIG. 2, is elliptical and has a major axis, 24, and a minor axis 26.

In a preferred embodiment, the actuator produces spray of the cyanocobalamin solution having a spray pattern ellipticity ratio of from about 1.0 to about 1.4 when measured at a height of 3.0 cm from the actuator tip. In a preferred embodiment less than 5% of the droplets of the cyanocobalamin solution are less than 10 µm in size, the spray pattern has a major axis and minor axis of 25 and 40 mm, respectively, 50% of the droplets are 26.9 µm or less in size, 90% of the droplets are 55.3 µm or less in size, and 10% of the droplets are 12.5 µm or less in size.

As noted above, the present invention provides improved methods and compositions for intranasal delivery cyanocobalamin to mammalian subjects for treatment or prevention of a variety of diseases, disorders and conditions. Examples of appropriate mammalian subjects for treatment and prophylaxis according to the methods of the invention include, but are not restricted to, humans and non-human primates, livestock species, such as horses, cattle, sheep, and goats, and research and domestic species, including dogs, cats, mice, rats, guinea pigs, and rabbits.

An initial therapy, the patient should receive daily intramuscular injections of 100 µg of cyanocobalamin for about 1 to 2 weeks, together with 1 to 5 mg of folic acid. Intramuscular injections of cyanocobalamin should not be greater than 100 µg as doses in excess of 100 µg are rapidly cleared from the plasma into the urine, and administration of larger amounts of vitamin B12 will not result in greater retention of larger amounts of the vitamin.

The cyanocobalamin nasal spray of the present invention is directed towards the maintenance of the hematological status of patients who are in remission following intramuscular vitamin B12 therapy. So instead of a once a month injection of 100 µg of cyanocobalamin, using the cyanocobalamin spray, the patient self-administers a dose of the nasal spray of the present invention containing 500 µg of cyanocobalamin once or twice a week. The maintenance therapy of the intranasal cyanocobalamin is for any patient that had been diagnosed with a vitamin B12 deficiency, but especially for those treated for pernicious anemia and dietary deficiency of vitamin B12 occurring in strict vegetarians, the so-called vegans who eat no animal products. Maintenance cyanocobalamin therapy using the cyanocobalamin solution of the present invention is also indicated for those afflicted with malabsorption of vitamin B12 resulting from structural or functional damage to the stomach, where intrinsic factor is secreted or to the ileum, where intrinsic factor facilitates B12 absorption. These conditions include tropical sprue and nontropical sprue (Idiopathic steatorrhea, gluten-induced enteropathy).

Maintenance cyanocobalamin therapy using the cyanocobalamin solution of the present invention is also indicated for those afflicted with malabsorption of vitamin B 12 resulting from inadequate secretion of intrinsic factor, resulting from lesion that destroys the gastric mucosa (ingestion of corrosives, extensive neoplasia), and a number of conditions associated with a variable degree of gastric atrophy (such as multiple sclerosis, human immunodeficiency viral (HIV) infection certain endocrine disorders, iron deficiency, and subtotal gastrectomy). Structural lesions that lead to B12 deficiency include ileitis, ileal resections, Crohn's disease and malignancies. Vitamin B12 deficiencies may also be the result of competition by intestinal parasites, and inadequate utilization of vitamin B12 occurring if antimetabolites for the vitamin are employed in the treatment of neoplasia.

The intranasal cyanocobalamin solution of the present invention can also be used for individual who require above normal levels of vitamin B12, due to for example pregnancy, thyrotoxicosis, hemolytic anemia, hemorrhage, malignancy, hepatic and renal disease.

As was stated above, the present invention provides for a stable pharmaceutical solution of cyanocobalamin suitable for intranasal administration, having a viscosity less than about 1000 cPs, wherein said intranasal solution of cyanocobalamin has when administered intranasally a bioavailability of at least 7% of the bioavailability of an intramuscular injection of cyanocobalamin. The intranasal formulation will generally be comprised of in addition to water and cyanocobalamin, a buffering agent to maintain the pH between 4 and 6 preferably about 5, a humectanct to inhibit drying of the mucous membranes and a preservative.

A preferred formulation is comprised of cyanocobalamin, citric acid, sodium citrate, and water wherein the viscosity is less than 1000 cPs, and wherein the solution of cyanocobalamin has a bioavailability of at least 7%, more preferably at least about 8, 9, 10, 11, 12% or more of the bioavailability of an intramuscular injection of cyanocobalamin.

Preferred compositions within the scope of this invention will contain a humectant to inhibit drying of the mucous membranes and to prevent irritation. Any of a variety of humectants can be used including, for example sorbitol, propylene glycol or glycerol. A preferred humectant is glycerin.

A preservative is generally employed to increase the shelf life of the compositions. Examples of preservative include benzyl alcohol, parabens thimerosal, chlorobutanol, benzethonium chloride and benzalkonium chloride. A preferred preservative is benzalkonium chloride. A suitable concentration of the preservative will be from 0.002% to 2% based upon the total weight, although there may be appreciable variation depending upon the agent selected.

A most preferred formulation has the concentration of cyanocobalamin at 0.5% (percent of total weight), citric acid 0.12%, sodium citrate 0.32%, glycerin 2.23%, benzalkonium chloride solution 0.02% and 96.79% water.

Other buffering agent combination include but are not limited to:

Monopotassium phosphate and disodium phosphate,

Potassium biphthalate and sodium hydroxide, and Sodium acetate and acetic acid.

Another embodiment of the present invention is a method for administering cyanocobalamin comprised of infusing the nose with an aqueous solution of cyanocobalamin, wherein the solution of cyanocobalamin has a viscosity of less than 1000 cPs, and wherein said solution of cyanocobalamin has a bioavailability of at least 7% relative to an intramuscular injection of cyanocobalamin. Preferably the bioavailability is at least about 8, 9, 10, 11, 12% or more of the bioavailability of an intramuscular injection of cyanocobalamin.

The present invention is further directed towards a method for elevating the vitamin B12 levels in the cerebral spinal fluid (CSF) comprising intranasally administering a solution of cyanocobalamin so as to increase the average ratio of vitamin B12 in the CSF to that in the blood serum (B12 CSF/B12 Serum×100) to at least about 1.1, wherein said solution of cyanocobalamin has a bioavailability of at least 7% relative to an intramuscular injection of a cyanocobalamin. In a more preferred embodiment the B12 CSF levels are increased so that the ratio of B12 in the CSF to the levels in the blood serum is at least 1.9.

This is a significant embodiment of the present invention because vitamin B12 deficiency can result in irreversible damage to the nervous system. Progressive swelling of myelinated neurons, demyelination, and neuronal cell death are seen in the spinal column and cerebral cortex. This causes a wide range of neurological signs and symptoms, including paresthesias of the hands and feet, diminution of vibration and position senses with resultant unsteadiness, decreased deep tendon reflexes, and, in the later stages, confusion, moodiness, loss of memory, and even a loss of central vision. The patient may exhibit delusions, hallucinations, or even an overt psychosis. Since the neurological damage can be dissociated from the changes in the hematopoietic, vitamin B12 deficiency must be considered as a possibility in elderly patients with dementia and psychiatric disorders, even if they are not anemic. Thus, the embodiment of the present invention directed towards increasing the level of vitamin B12 in the CSF can have tremendous benefit for neurological patients. Thus, intranasal administration of vitamin B12 can be used to treat such diseases as Alzheimer's disease, dementia, and multiple sclerosis.

Preferred formulations are the following: Cyanocobalmin Nasal Spray 500 mcg/0.1 mL
Formulation:

| Component. | Current Nasal Solution Quantity (% w/w) |
| --- | --- |
| Cyanocobalamin, USP | 0.50 |
| Citric acid anhydrous, USP | 0.12 |
| Sodium citrate dihydrate, USP | 0.32 |
| Glycerin, USP | 2.23 |
| Benzalkonium chloride (50%), NF | 0.04 |
| Purified water q.s. | 100.0 |

Alternative buffer systems and amounts that can be used for Cyanocobalamin Nasal Spray

| | Quantity (% w/w) |
| --- | --- |
| 1) Citric Acid-Phosphate buffer | |
| Citric Acid anhydrous, USP | 0.240 |
| Dibasic Sodium Phosphate anhydrous | 0.357 |
| 2) Acetate buffer | |
| Sodium Acetate anhydrous, USP | 0.220 |
| Acetic Acid, glacial, USP | 0.064 |
| 3) Phosphate buffer | |
| Monobasic Potassium Phosphate anhydrous, NF | 0.483 |
| Dibasic Sodium Phosphate anhydrous | 0.004 |

The intranasal formulations of the present invention can be administered using any spray bottle or syringe. A preferred nasal spray bottle is the, "Nasal Spray Pump w/Safety Clip, Pfeiffer SAP # 60548, which delivers a dose of 0.1 mL per squirt and has a diptube length of 36.05 mm. It can be purchased from Pfeiffer of America of Princeton, N.J.

The following examples are provided by way of illustration, not limitation.

Example 1

Comparison of Intranasal Cyanocobalamin Solution of the Present Invention with NASCOBAL® and Intramuscular Injections of Cyanocobalamin Introduction Nascobal® (Cyanocobalamin, USP) is a synthetic form of vitamin $B_{12}$ with equivalent vitamin $B_{12}$ activity. The chemical name is 5, 6-dimethyl-benzimidazolyl cyanocobamide. Currently, Nascobalo® (Cyanocobalamin, USP) is marketed as a self-administered nasal gel. The recommended dose of Nascobal® (Cyanocobalamin, USP) in subjects with vitamin $B_{12}$ malabsorption who are in remission following inject able vitamin $B_{12}$ therapy is 500-µg administered intranasally once weekly.

Vitamin $B_{12}$ deficiency has a number of causes, including malabsorption of vitamin $B_{12}$ resulting from structural or functional damage to the gastrointestinal system and dietary deficiency of vitamin $B_{12}$.

The purposes of this study are to compare the bioequivalence of vitamin $B_{12}$ nasal gel versus the nasal spray, and to evaluate the relative bioavailability of three preparations of vitamin $B_{12}$ in a fasted state in normal healthy male and female subjects.

Intranasal cyanocobalamin gel is approved for a dose of 500 µg. The current study also utilizes a cyanocobalamin nasal spray at the same 500 µg dose and an intramuscular dose of 100 µg.

Study Objectives

To compare the pharmacokinetic profile of a single intranasally-administered spray, single intranasally-administered gel (Nascobal®), and single intramuscular-administered vitamin $B_{12}$ in a fasted state in normal healthy male and female subjects.

Investigational Plan

Overall Study Design and Plan

This study was a single-site, open-label, 3-way (3-treatment, 6-sequence) crossover, pharmacokinetic study of vitamin B12 administered via intranasal (IN) spray (500-µg), IN gel (Nascobal®) (500-µg), and intramuscular (IM) injection (100-µ) in fasted normal healthy male and female subjects, as follows:

Treatment A: One IN spray administration of 500-µg vitamin $B_{12}$. The intranasal formulation was comprised of a preferred embodiment of the present invention and contained cyanocobalamin at a concentration of 0.5% (percent of total weight), citric acid 0.12%, sodium citrate 0.32%, glycerin 2.23%, 50% benzalkonium chloride solution 0.04% and 96.79% water.

Treatment B: One IN gel administration of 500-µg vitamin $B_{12}$ (Nascobal®).

Treatment C: One IM administration of 100-µg vitamin $B_{12}$.

Subjects were on a Vitamin $B_{12}$-free diet throughout each confinement period. Subsequent treatments will be dosed no sooner than 14 days following the preceding treatment dose administration.

Treatments

Treatments Administered

On Day 1 of Periods I, II, and III after an 8 hour fast, subjects received a single IN spray of 500-µg vitamin $B_{12}$ (Treatment A), a single IN gel of 500-µg vitamin $B_{12}$ (Nascobal®) (Treatment B), or a single IM administration of 100-µg vitamin $B_{12}$ (Treatment C) based upon a randomization generated by the PPD Development Biostatistician in one of six sequences. Following all periods, all subjects were to have received each treatment in a crossover manner. A washout period of 14 days separated the three dosing periods.

On the morning of Day 1, subjects assigned to Treatment A received a single IN spray administration of 500 µg of vitamin $B_{12}$. Subjects assigned to Treatment B received a single IN gel administration of 500 µg of vitamin $B_{12}$ (Nascobal®). Subjects assigned to Treatment C received a single IM administration of 100 µg of vitamin $B_{12}$. Doses were preceded by an overnight fast (i.e., at least 8 hours) from food (not including water) and were followed by a fast from food (not including water) for at least 4 hours post-dose.

While confined at the clinical site, subjects received a standardized vitamin $B_{12}$-deficient diet at scheduled times which did not conflict with other study-related activities. A registered dietician set up the diet, and the food staff maintained a diet diary. No dietary supplements were permitted during the study. Subjects abstained from consuming alcohol-containing, grapefruit-containing, or caffeine-containing foods or beverages for 72 hours prior to Check-in.

Study Variables

For each subject, the following pharmacokinetic parameters were calculated whenever possible, based on the serum concentrations of vitamin $B_{12}$ from Treatments A, B, and C according to the model independent approach: $C_{max}$, $T_{max}$, and $AUC_{0-t}$ Pharmacokinetic Measurements Blood samples for PK analysis of vitamin $B_{12}$ levels were collected via an indwelling catheter and/or via direct venipuncture using 5-mL yellow-top Vacutainer® Hemogard™ evacuated serum separator collection tube. Blood samples for PK analysis of vitamin $B_{12}$ levels were collected on Day −1 at 0, 6, and 12 hours and Day 1 at 0 hour (i.e., pre-dose); 30 minutes; 1, 1.5, 2, 4, 6, 8, 10, 12, 18, 24, 36, 48, 60, 72, 84 and 96 hours post-dose during each period.

Appropriateness of Measurements

The pharmacokinetic parameters used in this study were those typically used to assess bioequivalence. All assessments of bioequivalence were based on comparisons of $AUC_{0-t}$, $T_{max}$, and $C_{max}$ (test versus reference treatments).

AUC is a measure of the extent of drug bioavailability and reflects the total amount of drug that reaches the systemic circulation.

$C_{max}$ represents the maximum serum concentration obtained after drug administration and provides an indication that sufficient drug has reached the systemic circulation to provide a therapeutic response. In addition, $C_{max}$ provides warning of possible toxic drug levels.

$T_{max}$ was calculated and presented as median±range.

Pharmacokinetic Variables

For each subject, the following pharmacokinetic parameters were calculated, whenever possible, based on the serum concentrations of vitamin $B_{12}$ from Treatments A, B, and C, according to the model independent approach (Ref 1):

$C_{max}$ Maximum observed concentration.

$t_{max}$ Time to maximum concentration.

$AUC_{0-t}$ Area under the concentration-time curve from time 0 to the time of last measurable concentration, calculated by the linear trapezoidal rule.

Pharmacokinetic calculations were performed, using SAS (SAS Inst., Version 8.02).

Statistical Methods Planned in the Protocol and Determination of Sample Size

Statistical and Analytical Plans

Pharmacokinetic Analysis

Levels of vitamin $B_{12}$ in serum samples were measured as pg/mL. Serum concentration values below the quantifiable limits of detection were treated as zero. Actual sampling times, rather than scheduled sampling times, were used in all computations of the pharmacokinetic parameters. For ease of presentation, however, scheduled sampling times were used to present results in tables, listings, and figures.

From the concentration data, non-compartmental pharmacokinetic parameters ($AUC_{0-t}$, $C_{max}$, $T_{max}$ were calculated as described in Section 8.4.3.

Statistical Analysis

All statistical tests were conducted at the 0.05 significance level, unless otherwise specifically identified. Summary statistics of continuous parameters consisted of number (N), mean, median, SD, and range.

Descriptive statistics were obtained and tabulated by treatment for levels of vitamin $B_{12}$ at each time point and for the pharmacokinetic parameters calculated.

Bioequivalence was evaluated for the test (Treatment A—Nasal Spray) versus the reference (Treatment B-Gel). An analysis of variance (ANOVA, Ref. 2) was performed and the 90% confidence intervals were generated for the ratio of test/reference. $C_{max}$ and $AUC_{0-t}$, were natural log ($log_e$) transformed prior to analysis. The corresponding 90% confidence intervals for the geometric mean ratio were obtained by taking the antilog of the 90% confidence intervals for the difference between the means on the log scale.

It was assumed that the test (Treatment A) is non-inferior (with respect to the reference (Treatment B) if the lower bound of the 90% confidence intervals from $log_e$-transformed $C_{max}$, and $AUC_{0-t}$ were greater than or equal to 80%. If the lower bound of the 90% confidence intervals from $log_e$-transformed $C_{max}$ and $AUC_{0-t}$ were less than 80%, it was assumed that non-inferiority could not be established.

The sequence effect was tested using the mean square error (MSE) for subject within sequence as the error term. All other main effects were tested against the MSE from the ANOVA model.

Bioavailability was evaluated for the test (Treatments A and B—Nasal Spray and Gel, respectively) and the reference (Treatment C—IM) groups. Relative bioavailability was assessed by examining the 90% confidence intervals for the ratio of the test (Treatments A and B) group means relative to the reference (Treatment C) group mean.

For $T_{max}$, the analyses were run using Wilcoxon's matched pairs method to determine if differences exist between the test group and each reference group.

| SUMMARY - CONCLUSIONS |
|---|
| PHARMACOKINETIC RESULTS: |
| The relative bioavailability for the two IN formulations was 0.9715. Bioavailability when comparing Treatment A (spray) versus Treatment C (IM) was 0.6105, and 0.6284 when comparing Treatment B (gel) versus Treatment C (IM).<br>The pharmacokinetic profiles of the spray formulation and the gel formulation were similar for $C_{max}$ (1480 pg/mL, 1670 pg/mL, respectively) and $AUC_{0-t}$ (92000 pg * hr/mL, 97000 pg * hr/mL, respectively). Additionally, the median difference for $T_{max}$ between the spray and gel IN formulation was less than 15 minutes (−0.24). The $C_{max}$ value for the IM formulation was significantly higher than the $C_{max}$ values for the two IN formulations ($p < 0.0001$). Bioequivalence was established for the Vitamin $B_{12}$ IN spray with regard to the gel data based on $C_{max}$ and $AUC_{0-t}$. The 90% confidence intervals for the $\log_e$-transformed $C_{max}$ and $AUC_{0-t}$ for the spray and gel formulations fell within the range of 80% to 125%.<br>Additionally, non-inferiority can be assumed when comparing the two IN formulations because the lower bounds of the confidence intervals are greater than 80% for both $AUC_{0-t}$ and $C_{max}$. |
| CONCLUSIONS: |
| The relative bioavailability for the two IN formulations was 0.9715. Bioavailability for Treatment A (spray) versus Treatment C (IM) was 0.6105, and 0.6284 when comparing Treatment B (gel) versus Treatment C (IM).<br>The pharmacokinetic profiles of the spray formulation and the gel formulation are similar for $C_{max}$ (1480 pg/mL, 1670 pg/mL, respectively) and $AUC_{0-t}$ (92000 pg * hr/mL, 97000 pg * hr/mL, respectively). Additionally, the median difference for $T_{max}$ between the spray and gel IN formulation was less than 15 minutes (−0.24). The $C_{max}$ value for the IM formulation was significantly higher than the $C_{max}$ values for the two IN formulations ($p < 0.0001$).<br>Bioequivalence between the Vitamin $B_{12}$ spray formulation and the Vitamin $B_{12}$ gel formulation was established using $\log_e$-transformed 90% confidence intervals for $AUC_{0-t}$ and $C_{max}$. The 90% confidence intervals for the $\log_e$-transformed $C_{max}$ and $AUC_{0-t}$ for the spray and gel formulations fell within the range of 0.80 to 1.25. Noninferiority can be assumed for the two IN formulations (Treatment A versus Treatment B).<br>All Vitamin $B_{12}$ formulations were safe and well tolerated by healthy male and female volunteers. |

Example 2

We conducted a non-blinded, single dose, parallel group study to compare the uptake of Vitamin $B_{12}$ into the cerebrospinal fluid (CSF) after intranasal and intramuscular administration in healthy male and non-pregnant female volunteers. This study compared CSF levels to plasma levels produced by both formulations.

Thirty-six healthy male and non-pregnant female subjects, age 18 and over, were enrolled in the study. Eighteen subjects received a single intranasal dose of 500 mcg delivered as a 0.1 mL spray and eighteen subjects received a single intramuscular dose of 100 mcg delivered intramuscularly. Each subject visited the clinical site three times in a one-month period. These visits consisted of a screening visit, one dosing visit and a final visit.

After each dosing, each subject underwent lumbar puncture only once, with the retrieval of a total 4.0 mL of CSF (4 tubes, 1.0 mL per tube). One third of the subjects had a CSF sample collected at 60 minutes post dosing, one third of subjects had a CSF sample collected at 90 minutes post dosing, and one third of subjects had a CSF sample collected at 120 minutes post dosing.

In addition to the above, on the day of dosing 7 mL blood samples were drawn before dosing and post dosing at 5, 10, 15 and 20 minutes, and at 0.5, 1, 1½, 2, 3, 4, 6, and 8 hours post-dose (prior to discharge).

The cerebrospinal fluid was evaluated for total Vitamin $B_{12}$ content. It was the objective of the study described herein to measure the amount of Vitamin $B_{12}$ present in the blood and CSF following intramuscular (IM) and nasal administration.

Reference and Test Products

Reference Product: Cyanocobalamin 100 mcg intramuscular injection.

Cyanocobalamin Injection, USP is a sterile solution of cyanocobalamin (Vitamin $B_{12}$) for intramuscular or subcutaneous injection. Each mL contains 1,000 mcg cyanocobalamin.

Test Product: Vitamin $B_{12}$ Nasal Spray=500 mcg/0.1 mL spray. The cyanocobalamin intranasal aqueous solution was a preferred formulation of the present invention and contained cyanocobalamin at a concentration of 0.5% (percent of total weight), citric acid 0.12%, sodium citrate 0.32%, glycerin 2.23%, 50% benzalkonium chloride solution 0.04% and 96.79% water.

Vitamin $B_{12}$ Nasal Spray is supplied as a 2.3 mL bottle to deliver one dose: 500 mcg/0.1 mL per dose.

Before intranasal dosing, all subjects were be given an orientation of the proper dosing technique and general conduct of the study.

The subject was instructed to gently blow his/her nose. The subject remained in a seated position, and the primed IN applicator was inserted into the nostril by the subject, under the direction of the study staff. During dosing, the contralateral nostril was closed with the forefinger. Subjects will also be instructed to tilt their heads slightly back for dosing and to return their heads to an upright position while sniffing in gently immediately following dosing. A 0.1 mL dose of vitamin $B_{12}$ spray will be released into the nasal cavity. (A dose is a single application to one nostril.) Subjects must inform the staff if they sneeze or if the product drips out of their nose. Subjects will not be re-dosed if they sneeze or if the product drips out of their nose. Subjects will be instructed to refrain from blowing their nose for 1 hour following IN treatment.

After dosing, each subject underwent lumbar puncture, involving the retrieval of 4.0 mL of CSF (4 tubes, 1.0 mL per tube). One third of subjects from each group will have a CSF sample collected at 60 minutes post dosing, one third of subjects will have a CSF sample collected at 90 minutes post dosing, and one third of subjects will have a CSF sample collected at 120 minutes post dosing.

At the appropriate time after dosing, the Investigator positioned the patient appropriately in order to proceed with lumbar puncture. The lumbar area was prepared and draped in the usual aseptic fashion. Local anesthesia was utilized (1% xylocaine, 1-5 mL). Upon reaching a state of adequate anesthesia, a spinal needle (20 or 22 G) was introduced into the spinal canal, at the level deemed appropriate by the Investigator. The CSF samples were collected 60, 90 or 120 minutes after administration. A total of 4.0 mL of CSF were collected from each patient, and distributed into 4 separate collection tubes. The tubes were appropriately labeled with a patient identifier and submitted for bioanalytical analysis. Upon completion of CSF collection, the spinal needle was removed.

The levels of vitamin B12 were determined in both the CSF and blood serum using Vitamin $B_{12}$ concentrations in the CSF will be analyzed for Qualitative determination of Vitamin $B_{12}$ using a validated TOSOH Nex. 1A procedure.

Results and Conclusion

The data showed that the ration of vitamin $B_{12}$ to serum was higher in those individuals receiving intranasal administration of vitamin $B_{12}$ than those receiving intramuscular injections of vitamin $B_{12}$.

The average ratio ($B_{12}$ CSF/$B_{12}$ Serum×100) ranged from 1.1 to 1.9 for those individuals receiving intranasal administration of vitamin $B_{12}$ while those who received intramuscular injections of vitamin B12 had an average ratio ranging from 0.17 to 0.24. This is a surprising result in that intranasal administration only has about a 7-12% bioavailability in the blood serum relative to intramuscular injection of vitamin $B_{12}$. This indicates that intranasal administration of vitamin $B_{12}$ reaches the CSF much more effectively than by intramuscular injection.

Example 3

Production of a Cyanocobalamin Solution

A 4000 g batch of a cyanocobalamin solution of the present invention, which had a concentration of 500 mcg/0.1 g of solution.

| Starting Materials I. Formula Record | |
|---|---|
| Ingredient Name | Theoretical Weight (Grams) |
| Cyanocobalamin, USP | 20.0 |
| Citric Acid, USP (Anhydrous) | 4.8 |
| Sodium Citrate, USP (Dihydrate) | 12.8 |
| Glycerin, USP | 89.2 |
| Benzalkonium Chloride Solution, NF (50%) | 1.6 |
| Purified Water, USP | 3871.6* |

The 3871.6 grams of water was placed in a stainless steel container, which had been placed on a hot plate. The water was heated to about 30° C. and stirred. Into the heated water was added 12.8 g of sodium citrate while the water was being stirred at 300 rpm for 5 minutes. The 4.8 g of citric acid was then added and stirred for 10 minutes. Into this mixture was added 20.0 g of cyanocobalamin and stirred for 30 minutes at 30° C. at 300 rpm. The hot plate was then turned off. The 89.2 g of glycerin was added and stirred for 5 minutes at 300 rpm. Into the cyanocobalamin solution was then added 1.6 g of an aqueous solution containing 50% by weight of Benzalkonium Chloride was added to the solution and stirred for 5 minutes at 300 rpm. The pH was then measured and adjusted if the pH was not with the 4.5-5.5 range. Additional water was added to bring the weight of the solution to 4000 g.

Example 4

This example describes a pharmaceutical composition product comprising an aqueous solution formulation of salmon cyanocobalamin at a concentration sufficient to produce therapeutically effective plasma concentrations and an actuator to produce an aerosol of said solution, wherein the spray pattern ellipticity ratio of said aerosol is between 1.00 and 1.40 when measured at a height of 30 cm distance from the actuator tip.

The volume of the aerosol can be between about 5 microliters and 1.0 ml, preferably between 20 and 200 microliters.

This test method describes the procedure for characterizing plume geometry of the cyanocobalamin nasal solution formulations using the SprayView NSP system. The plume geometry is characterized using a SprayView High Speed Optical Spray Characterization System (SprayView NSP) with Integrated SprayView NSx actuation station (Image Therm Engineering, Inc., Sudbury, Mass.) according to the methods described in U.S. Pat. No. 6,665,421 and U.S. patent Application Publication No. 20030018416 published Jan. 23, 2003.

Using the formulation of table 1 the spray characterization and droplet size of the formulation in both a 3 mL bottle both having a nasal Spray Pump w/Safety Clip, Pfeiffer SAP # 65550, which delivers a dose of 0.1 mL per squirt and has a diptube length of 36.05 mm.

The droplet size data are shown in the following table.

| Droplet Size for Nasal Spray Bottle and Pfeiffer SAP # 60548 | | | | | |
|---|---|---|---|---|---|
| | $D_{10}$ | $D_{50}$ | $D_{90}$ | Span | % <10 micrometer |
| 1 mL Salmon cyanocobalamin | 12.5 | 26.9 | 55.3 | 1.6 | 5.1 |

Below are listed the spray pattern results

| Spray Pattern | | Major Axis | Minor Axis | Ellipticity Ratio |
|---|---|---|---|---|
| active | 3 mL | 35.3 mm | 30.8 mm | 1.14 |

What is claimed is:

1. A method for administering cyanocobalamin comprised of providing an aqueous solution of cyanocobalamin wherein said aqueous solution of cyanocobalamin is comprised of cyanocobalamin at a concentration of about 0.5% of total weight of solution, citric acid at a concentration of about 0.12%, sodium citrate at a concentration of about 0.32%, glycerin at a concentration of about 2.23%, benzalkonium chloride at concentration of about 0.02% and water, wherein said solution of cyanocobalamin is suitable for intranasal administration and has a viscosity less than about 1000 cPs, with the proviso that the solution of cyanocobalamin contains no mercury or mercury-containing compounds, and wherein the cyanocobalamin solution is administered into a nose of an individual through an actuator tip as a spray, wherein the spray has a spray pattern ellipticity ratio of from about 1.0 to about 1.4 when measured at a height of 3.0 cm from the actuator tip.

2. The method of claim 1 wherein the cyanocobalamin spray produces droplets of the solution, wherein less than 5% of the droplets are less than 10 μm in size.

3. The method of claim 1 wherein the cyanocobalamin spray produces droplets of the solution, and wherein 50% of the droplets are 26.9 μm or less in size.

4. The method of claim 1 wherein the cyanocobalamin spray produces droplets of the solution, and wherein 90% of the droplets are 55.3 μm or less in size.

5. The method of claim 1 wherein the cyanocobalamin spray produces droplets of the solution, and wherein 10% of the droplets are 12.5 μm or less in size.

6. The method of claim 1 wherein the spray has a spray pattern major axis and a minor axis of about 25-40 mm each.

* * * * *